United States Patent
Reng

(10) Patent No.: US 10,022,129 B2
(45) Date of Patent: Jul. 17, 2018

(54) TOOL FOR INSERTION INTO A SURGICAL SAW, AND METHOD FOR MILLING A GROOVE

(71) Applicant: Wolfgang Reng, Garmisch-Partenkirchen (DE)

(72) Inventor: Wolfgang Reng, Garmisch-Partenkirchen (DE)

( * ) Notice: Subject to any disclaimer, the term of this patent is extended or adjusted under 35 U.S.C. 154(b) by 232 days.

(21) Appl. No.: 14/994,784

(22) Filed: Jan. 13, 2016

(65) Prior Publication Data

US 2016/0135814 A1    May 19, 2016

Related U.S. Application Data

(63) Continuation of application No. PCT/EP2014/064312, filed on Jul. 4, 2014.

(30) Foreign Application Priority Data

Jul. 15, 2013   (DE) .................. 10 2013 107 485

(51) Int. Cl.
| | | |
|---|---|---|
| *A61B 17/14* | (2006.01) | |
| *A61B 17/32* | (2006.01) | |
| *B26B 9/02* | (2006.01) | |

(52) U.S. Cl.
CPC ............ *A61B 17/144* (2016.11); *A61B 17/14* (2013.01); *A61B 17/142* (2016.11); *A61B 17/32002* (2013.01); *B26B 9/02* (2013.01)

(58) Field of Classification Search
CPC ..... A61B 17/14; A61B 17/142; A61B 17/144; A61B 17/32002; B26B 9/02
See application file for complete search history.

(56) References Cited

U.S. PATENT DOCUMENTS

| 67,369 | A | | 7/1867 | Stephenson | |
|---|---|---|---|---|---|
| 5,448,833 | A | * | 9/1995 | Coon ..................... | B23D 51/01 30/142 |
| 5,824,098 | A | * | 10/1998 | Stein ................. | A61B 17/1728 623/20.18 |
| 7,527,628 | B2 | * | 5/2009 | Fletcher ................ | B23D 51/10 606/177 |

(Continued)

FOREIGN PATENT DOCUMENTS

| EP | 1 974 679 A2 | 10/2008 |
|---|---|---|
| WO | 9301751 A1 | 2/1993 |

*Primary Examiner* — Larry E Waggle, Jr.
(74) *Attorney, Agent, or Firm* — Hackler Daghighian Martino & Novak

(57) ABSTRACT

A tool for insertion into a surgical saw includes a holder area for the saw and a head which is movable in oscillation by the surgical saw along a work direction where the head has a plurality of teeth which are arranged behind one another in the work direction. A first and second tooth each contains a first shaving surface for shaving off bone material oriented transversely to the work direction and a second pressing surface for pressing on bone material which pressing surface adjoins the shaving surface. The shaving surface, in relation to the work direction, is more inclined than the pressing surface. The two teeth are oriented with their shaving surface and pressing surface opposite each other so during oscillation the shaving surface of the tooth lying ahead in work direction and the pressing surface of the tooth lying therebehind in work direction are in operation.

17 Claims, 2 Drawing Sheets

(56) References Cited

U.S. PATENT DOCUMENTS

| | | | |
|---|---|---|---|
| D622,383 S | 8/2010 | Fisher | |
| D622,386 S | 8/2010 | Fisher | |
| 8,206,392 B2 * | 6/2012 | Fisher | A61B 17/144 606/176 |
| 2004/0243136 A1 * | 12/2004 | Gupta | B23D 61/006 606/82 |
| 2008/0243125 A1 * | 10/2008 | Guzman | A61B 17/142 606/82 |
| 2009/0093814 A1 | 4/2009 | Fletcher et al. | |
| 2010/0292701 A1 | 11/2010 | Fisher et al. | |
| 2011/0092975 A1 | 4/2011 | Fisher | |
| 2012/0130380 A1 | 5/2012 | Babaev | |

* cited by examiner

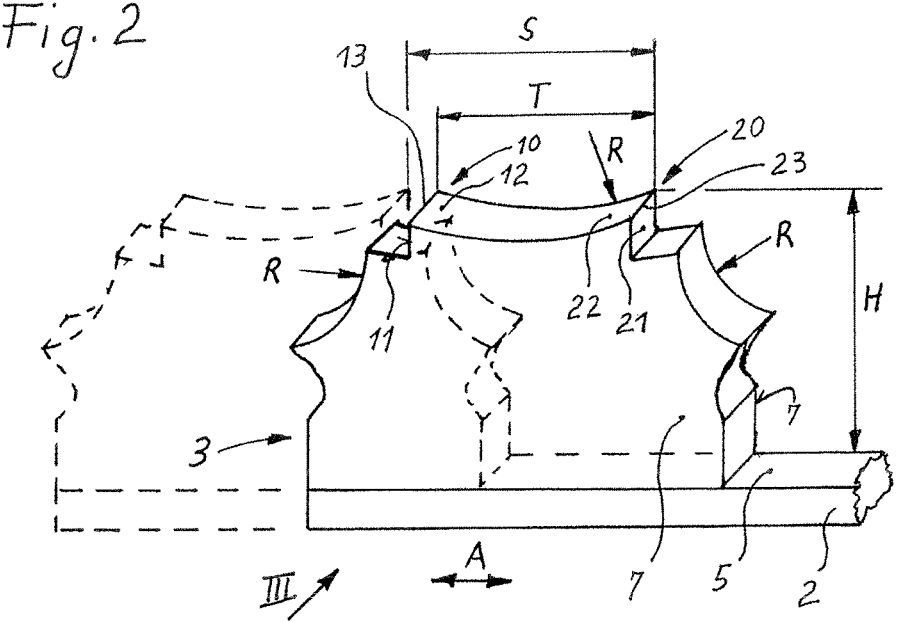
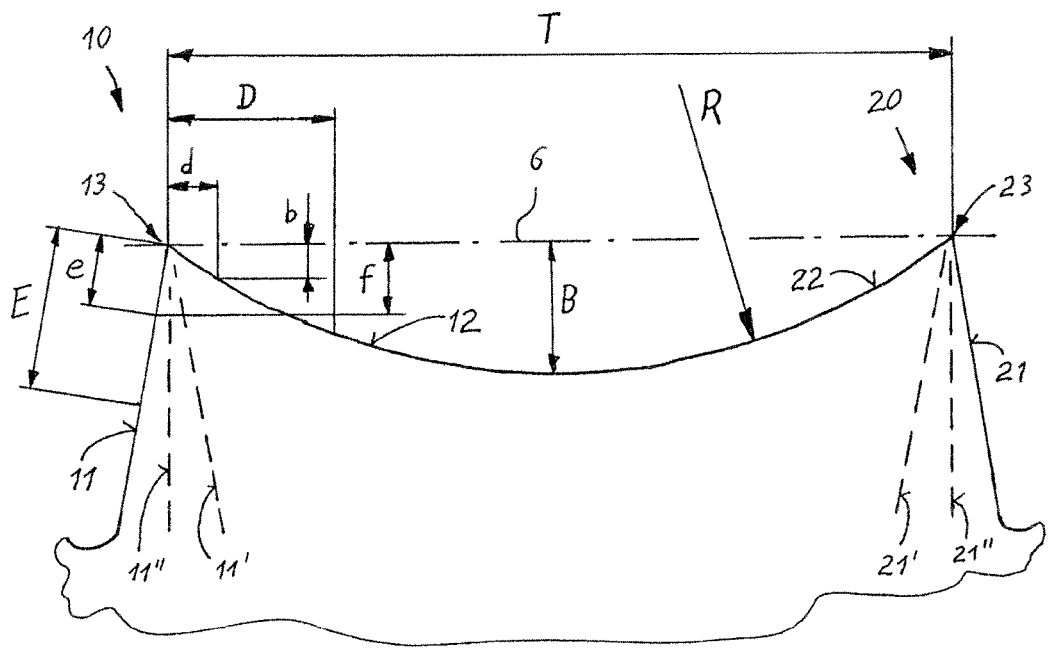

TOOL FOR INSERTION INTO A SURGICAL SAW, AND METHOD FOR MILLING A GROOVE

CROSS-REFERENCE TO RELATED APPLICATIONS

This continuation application claims priority to PCT/EP2014/064312 filed on Jul. 4, 2014 which has been published as WO 2015/007546 A1 and also the German patent number 10 2013 107 485 filed on Jul. 15, 2013, the contents of which are fully incorporated herein with these references.

FIELD OF THE INVENTION

The invention relates to a tool for insertion into a surgical saw. A tool for insertion into a surgical saw with a holder area adapted to a tool holder of the surgical saw and with a head which is movable in oscillation by the surgical saw along a work direction and has a plurality of teeth which are arranged behind one another in the work direction, is known from U.S. Pat. No. D622,383 S and U.S. Pat. No. D622,386 S. The known tool has at its head two parallel saw blades with a plurality of teeth being off-set with respect to one another. The two saw blades are arranged at a distance from one another, so that two parallel slots can be sawn by the tool.

BACKGROUND OF THE INVENTION

The tool is an operation instrument in human medicine. It can be used in the preparation of the osseous support in the implantation of an artificial joint replacement, in particular in the case of knee joints. Endoprostheses are often secured in grooves which are introduced into the bone. The implant is subsequently cemented into the groove or is driven into the groove in a cement-free manner. In particular in the case of the cement-free fastening, the groove in the bone must be prepared very precisely.

In order to increase the precision in the preparation of the groove in the bone, it is also known to fasten a template on the bone, which template has a slit which corresponds in its length and width to the length and width of the groove which is to be sawn out in the bone lying beneath. The known tool, mentioned in the introduction, having the two parallel saw blades at its head, has a width there which corresponds to the width of the groove which is to be sawn out. The length of the saw blades is shorter than the groove which is to be sawn out. The known tool is inserted into a surgical jigsaw, is set by the latter into a linear oscillating movement and is introduced with its saw blades, arranged at the head, into the slit of the template which is fastened on the bone. The head of the tool with the saw blades projects over a guide surface provided on the tool, so that the guide surface rests on the surface of the template when the saw blades have reached a particular depth in the bone. With the known tool, therefore, two parallel slits can be sawn into the bone, the distance of which corresponds to the desired groove width, with their length corresponding to the desired groove length and their depth corresponding to the desired groove depth. Between the two slits, a bone strip remains, running in longitudinal direction of the groove. In the known method, this bone strip is subsequently removed by a hand-operated, depth-limited special chisel. The special chisel must be operated manually in a drawing and pushing manner through the groove, wherein a lateral tilting of the special chisel can occur. The freehand preparation of the groove with the special chisel can consequently lead to an increased variance in the bone groove dimensions. In particular in the case of structural changes to the bone in the region of the groove (osteosclerosis, calluses, foreign bodies, cysts or osteoporosis), a distinctly altered effort of force can occur during operation of the special chisel, through which the accuracy of preparation is reduced. The known tool is, in addition, only permitted for one-time use, so that for each operation a new saw tool is necessary and thereby high operation costs arise.

It is an object of the present invention to provide a tool for insertion into a surgical saw which has improved characteristics. This object has been achieved by a tool having the features of the claims.

SUMMARY OF THE INVENTION

The tool according to the invention has a holder area adapted to a tool holder of a surgical saw, and a head which is movable in oscillation by the surgical saw along a work direction. The tool is suitable for various surgical saws, namely both for jigsaws, which carry out a linear oscillating movement, and also for saws which set the tool into an oscillating pivoting movement. A plurality of teeth are provided on the head of the tool. At least two of the teeth are arranged behind one another in the work direction and can be moved forward and backward in an oscillating manner by the saw along the work direction. The head of the tool has a first and a second tooth for the milling off of bone material. For this, the head can be fed to the bone in a feed movement oriented transversely to the work direction. Each of the teeth contains a first surface for shaving off bone material, which surface is oriented transversely with respect to the direction of the oscillating movement, and is referred to below as the "shaving surface". Each of the teeth contains a second surface for pressing on bone material, which second surface adjoins the shaving surface and is referred to below as the "pressing surface". The shaving surface, in relation to the work direction, is more strongly inclined than the pressing surface. The two teeth are oriented with their shaving surface and their pressing surface opposite each other, such that, during a movement of the head in the work direction, at any one time the shaving surface of the tooth lying ahead in work direction and the pressing surface of the tooth lying therebehind in work direction are in operation.

The invention further relates to a method for milling a groove into a bone with a tool inserted into a surgical saw, which tool has a head with a plurality of teeth, which head is moved in oscillation forward and backward by the saw along a work direction. On the forward movement of the head, a shaving surface, lying ahead in work direction, of a first tooth shaves off bone material, and a pressing surface of a second tooth, lying behind the shaving surface of the first tooth, presses bone material against the bone. On the backward movement of the head, a shaving surface of the second tooth, lying ahead in working direction, shaves off bone material, and a pressing surface of the first tooth, lying behind the shaving surface of the second tooth, presses bone material against the bone. The method according to the invention can also be carried out on a dead human or animal body or on a bone outside the living human or animal body. It can be carried out for example for the purposes of the training of surgeons, the testing of a tool according to the invention and/or the testing of an implant.

The invention may have (but which are not necessary) substantial advantages:

The tool according to the invention can be operated like a saw blade on a mechanical surgical saw, in particular a surgical jigsaw. Structural alterations to the surgical saw are not necessary.

In contrast to the known saw blades, the bone material is not cut up. The tool according to the invention therefore does not have any saw teeth being off-set with respect to one another. The bone material is not cut by the configuration according to the invention, but rather is shaven off or milled off. Thereby, a very good and clean surface of the bone can be achieved. The shaving function carried out by the shaving surface during the forward movement in the work direction is therefore comparable, rather, with a bone planer.

With the tool according to the invention, the shaven off bone particles are not, as in the case of conventional saw blades, to be conveyed out from the groove. Rather, the shaven off bone material is to be pressed by the pressing surfaces onto the bone in the region of the groove edges. By the pressing in of bone particles into the groove edges, the bone material is compacted in the region of the groove edges. Through the compacting, an increase in the stability of the bone material can be achieved, which leads to an improved durability and increased load carrying capacity of the implant which is inserted into the groove.

Through the fact that the two teeth are oriented with their shaving surface and their pressing surface opposite each other, it is ensured that both in the forward movement of the head and also in the backward movement of the head respectively a shaving surface and a pressing surface, lying therebehind in work direction, works. The pressing surface is inclined relatively slightly in relation to the work direction, in order to ensure a good pressing or "spreading" of the bone material onto the osseous contact surface.

With the tool according to the invention, the required groove can be milled in the bone in one working step. The imprecise final preparation with the special chisel is no longer necessary. Hereby, a very high degree of accuracy is achieved in the groove preparation and the entire operation time is shortened. The variance of the bone groove dimensions can be reduced both in the homogeneous spongiosa bone and also in the non-homogeneous bone. Thereby, to a greater extent than hitherto, a cement-free inserting of the implant can be carried out.

Through the tool according to the invention, the general and the specific complication rate can be reduced. This means in particular a reduced rate of wound infections, reduced post-operative need for analgesics and infusion, and a shortened convalescence duration. The direct operation costs and the general hospital costs can be reduced.

The tool according to the invention is in particular very well suited for the implantation of the tibial portions of a knee joint implant of the Biomet company, Warsaw, Ind., USA, which is known as the "Oxford Unicondylar Knee System", and in which hitherto the tool described in the introduction having the two parallel saw blades is used. The advantages of the invention become evident here to a particular extent. The tibial portion of the Oxford unislide endoprosthesis has a perforated fin for anchoring in the tibial spongiosa bone support. Viewed transversely to the longitudinal direction of the groove, the anchoring fin is rounded at the front and rear end. With the tool according to the invention, a groove can be milled which is adapted precisely to these roundings of the fin. The shaving out of the groove in the known method at the front and rear end of the groove by the hand-operated special chisel in a way deeper than required by the contour of the anchoring fin is dispensed with. The seat of the anchoring fin in the groove is thereby improved.

The tool according to the invention can particularly be permitted for a surgical multiple use. For this, the tool can be embodied in one piece. Particularly, it can be highly polished. The tool is embodied free of undercut and has no holes, cavities or other contours in which bone- and tissue residues accumulate. Hereby, a machine-made cleaning within sterile material processing is made possible. Furthermore, all surfaces are visible for quality inspection during sterilization. The tool can consist of a stainless chromium steel ("surgical steel"). A martensitic chromium steel with a chromium content of at least 18% is particularly suited, as is obtainable for example under the standardized material number 1.4112. For an authorization for multiple use, the tool meets the relevant regulations, in particular the directive 93/42/EEC, the Medical Devices Act, the Medical Devices Marketing Regulations and the guidelines for re-use drawn up by the Robert Koch Institute.

In a further embodiment of the invention, each of the teeth can contain an edge, formed at the transition from the shaving surface to the pressing surface, which edge is designated below as the "main cutting edge". The main cutting edge of the first tooth can run parallel to the main cutting edge of the second tooth. The main cutting edge can have an angle of at least 75° to the work direction, in particular it can run perpendicularly to the work direction. The main cutting edge particularly runs in a straight line. The distance of the main cutting edge of the first tooth to the main cutting edge of the second tooth—measured parallel to the work direction—is in particular at the most as great as the work stroke of the saw, for which the tool is intended. The distance of the main cutting edge of the first tooth to the main cutting edge of the second tooth can be 2 mm to 10 mm, in particular 3 mm to 8 mm. Hereby, a particularly suitable tooth shape can be achieved, in which the teeth are not off-set with respect to one another. The surface created by the tool in the bone groove can thereby be improved.

The tool can have a guide surface for delimiting the milling depth of the tool in the bone material, wherein the head of the tool projects over the guide surface, and the guide surface is oriented parallel to the work direction. Viewed in the work direction, the guide surface can extend on both sides of the head. The height of the main cutting edges over the guide surface conforms to the desired groove depth and can be 8 mm to 20 mm, in particular 10 mm to 15 mm. Before the milling of the groove in the bone, a milling template containing a slit can be placed onto the bone and can be fixed there. Subsequently, the head of the tool can be introduced with a feed movement oriented transversely to the work direction into the slit of the milling template, in order to mill a groove into the bone material lying under the milling template, which groove corresponds in its length to the length of the slit in the milling template and corresponds in its width to the width of the head of the tool. The guide surface serves for delimiting the feed movement of the head in the depth direction of the groove which is to be milled, in particular for the applying of the tool onto the milling template being placed onto the bone. Particularly, the width of one of the main cutting edges transversely to the work direction can correspond to the width of the groove which is to be milled. Hereby, the groove can be prepared in its full width by the tool according to the invention in only one working step, so that an additional working step with a special chisel is no longer necessary.

When, after the milling of the groove, an implant is inserted into the groove, the groove width can be milled as a function of the width of the part of the implant which is to be inserted into the groove and as a function of the type of anchoring of the implant. In the case of an anchoring in which the implant is cemented in, the groove is milled wider than the width of the part of the implant which is to be inserted into the groove. In the case of a "fit and fill" anchoring, which is suitable for a cemented and cement-free anchoring, the groove width corresponds to the width of the part of the implant which is to be inserted into the groove. In the case of a "press fit" anchoring, in which the implant is inserted with a clamping fit without cement, the groove is milled narrower than the width of the part of the implant which is to be inserted into the groove. In the case of a "press fit" anchoring, the groove can be milled 0.1 mm to 0.4 mm, in particular 0.3 mm, narrower than the width of the part of the implant which is to be inserted into the groove, for example the anchoring fin. In particular in the case of the cement-free fastening, the groove must be neither too wide—then the anchoring fin would not sit securely—nor too narrow—then the bone, particularly if it is altered sclerotically, could receive cracks during the pressing in of the anchoring fin. Through the said dimensions, a well-suited press fit between groove and anchoring fin can be achieved, which enables a reliable cement-free fastening of the implant in the groove.

In a further embodiment of the invention, the pressing surface in a section adjoining the main cutting edge can change its distance with respect to a reference line at most by 0.2 mm, in particular by at most 0.17 mm, when the distance of the pressing surface with respect to the reference line is measured at two locations which are spaced 0.2 mm from one another along the reference line. The reference line is a straight line which is applied parallel to the work direction onto the main cutting edge of the first tooth and/or the main cutting edge of the second tooth. The reference line can thus be applied to the main cutting edge of the first tooth and the main cutting edge of the second tooth, so that during the oscillating movement of the head in the work direction a defined location on the bone is covered both by the contact point of the reference line with the main cutting edge of the first tooth and also by the contact point of the reference line with the main cutting edge of the second tooth. The reference line can lie in a reference plane which intersects the main cutting edge of the first tooth and the main cutting edge of the second tooth. The reference plane is a plane lying parallel to the work direction, which plane lies, at the same time, parallel to a feed movement by which the teeth are able to be fed to the bone transversely to the work direction during the milling of the groove. The reference plane can lie perpendicularly to the guide surface. The reference line can be a straight line which is applied in the reference plane onto the main cutting edge of the first tooth and the main cutting edge of the second tooth. The section of the pressing surface adjoining the main cutting edge extends along the reference line up to a distance of 0.5 mm, in particular 1 mm, from the main cutting edge. The shaving surface, in a section adjoining the main cutting edge, can change its distance with respect to the reference line at least by 0.18 mm, in particular by at least 0.19 mm, when the distance of the shaving surface with respect to the reference line is measured at two locations which are spaced 0.2 mm apart from one another along the shaving surface. The section of the shaving surface adjoining the main cutting edge extends along the shaving surface up to a distance of 0.5 mm, in particular 1 mm, from the main cutting edge. The distance of the pressing surface with respect to the reference line and the distance of the shaving surface with respect to the reference line are measured perpendicularly to the reference line. The shaving surface and/or pressing surface can run in a straight line or in a curved manner.

Through the difference measurement of the distance with respect to the reference line, carried out at two locations spaced apart from one another, a value is defined for the inclination of the shaving surface or respectively of the pressing surface with respect to the work direction, which is independent of a curvature of the pressing surface or of the shaving surface. The inclination of the shaving surface or respectively of the pressing surface determines how intensively the shaving surface or respectively the pressing surface, on a displacement of the head by a predetermined path in the work direction, changes its distance from the reference line, and how intensive the shaving or respectively pressing effect of the respective surface is. The tooth contour between the main cutting edge of the first tooth and the main cutting edge of the second tooth can have a distance with respect to the reference line which is at most 25%, in particular 10% to 20% of the distance, measured along the reference line, from the main cutting edge of the first tooth to the main cutting edge of the second tooth. It has been found, surprisingly, that a particularly good surface quality of the groove surface can be achieved with a tool having the said dimensions.

In further configuration of the invention, the shaving surface can be a planar surface which has an angle of at least 75°, in particular of at least 85°, to the work direction. The planar shaving surface can be oriented perpendicularly to the work direction, i.e. can have the greatest possible angle of 90° to the work direction. The angle between the planar shaving surface and the work direction can be measured in the reference plane, whilst at the same time the planar shaving surface runs perpendicularly to the reference plane.

In a further embodiment, the pressing surface of the first tooth and the pressing surface of the second tooth can be curved in a concave manner. In a sectional view, in which the section plane runs parallel to the reference plane through the main cutting edge, the pressing surface can have a radius of curvature of at least 2 mm, in particular of 3 mm to 10 mm. Particularly, the radius of curvature is 4 mm to 6 mm. Hereby, a particularly good pressing of shaven off bone material onto the bone can be achieved. In particular, the pressing surface of the first tooth and the pressing surface of the second tooth can be formed by the surface of a circular cylinder. Here, the pressing surface of the first tooth can continue in a kink-free manner into the pressing surface of the second tooth. The centre line of the circular cylinder can be oriented perpendicularly to the work direction. It can lie perpendicularly to the reference plane, and in particular also parallel to the guide surface. The pressing surfaces can run perpendicularly to the reference plane. The circular cylinder can have a diameter of at least 5 mm, in particular of 7 mm to 12 mm.

In particular, the head of the tool can have lateral surfaces which are oriented parallel to the work direction. Particularly, the head has planar lateral surfaces. The lateral surfaces can be perpendicular to the guide surface. In a sectional view, in which the section plane runs perpendicularly to the work direction through the head, each tooth can have a rectangular cross-section. Through such a configuration of the lateral surfaces of the head, a good compacting of the bone material can also be achieved on the lateral surface of the groove.

In a further embodiment of the invention, the tool can contain a body with a longitudinal direction, wherein at a first end of the body the head of the tool is arranged and wherein at a second end of the body a holder area is arranged, adapted to a tool holder of a surgical jigsaw, via which holder area the tool is movable in a linear manner by the surgical jig saw in a work direction oriented parallel to the longitudinal direction of the body. The holder area of the tool can have a surface section running parallel to the work direction.

BRIEF DESCRIPTION OF THE DRAWINGS

Further advantages and features of the invention will become more readily apparent from the following description of an example embodiment in conjunction with the figures.

There are shown:

FIG. 2 is a diagrammatic oblique view onto the head of a tool according to the invention; and FIG. 3 is a highly enlarged view in the direction of the arrow III of FIG. 2 onto the first and the second tooth of the head.

DETAILED DESCRIPTION OF THE PREFERRED EMBODIMENTS

Figure 1:
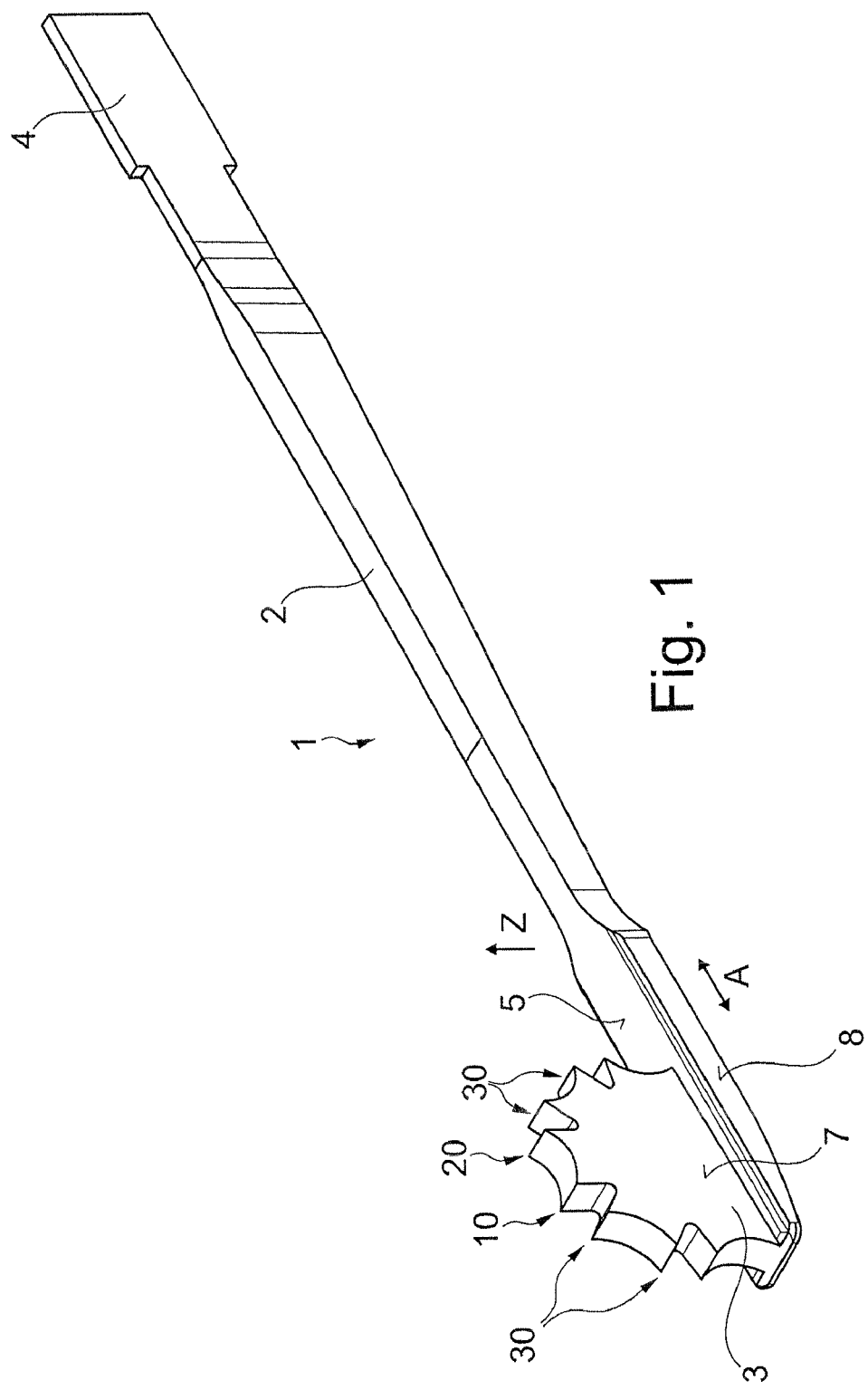
FIG. 1 is an oblique view of a tool according to the invention.

In FIG. 1 a tool 1 for insertion into a surgical jigsaw is illustrated. The tool 1 has an elongated body 2 with a longitudinal direction. A head 3 is arranged at a first end of the body 2. At a second end of the body 2, a holder area 4 is arranged, which is adapted to a tool holder of the surgical jigsaw. The tool 1 is inserted with the holder area 4 into the tool holder of the surgical jigsaw and, when the surgical jigsaw is switched on, is moved forward and backward by the surgical jigsaw parallel to the longitudinal direction of the body 2. The direction of the oscillating movement of the tool 1 is indicated in FIG. 1 by the double arrow marked by the letter A and is designated as the work direction. The head 3 has a first tooth 10 and a second tooth 20 for milling off bone material. The configuration of the teeth 10 and 20 is explained in further detail below. In addition to the teeth 10 and 20, the head 3 can have further teeth 30, which are configured in a similar manner to the teeth 10 and 20. On the body 2 a guide surface 5 is provided for delimiting the milling depth of the tool 1 in the bone material. The head 3 projects over the guide surface 5. The guide surface 5 surrounds the head 3 on three sides. The guide surface 5 is parallel to the work direction A.

The tool 1 illustrated in FIG. 1 can be used in a method for milling a groove into any desired bone. It is particularly well suited for milling a groove into a tibia bone and is therefore described below by way of example in this application. In preparatory method steps, a plateau is prepared on the tibia. On the plateau a milling template, containing a slit, is placed and is fixed there. The tool 1, inserted into the jigsaw, is introduced, with a running jigsaw, with the head 3 into the slit of the milling template, then the head 3 is fed to the bone with a feed movement Z oriented transversely to the work direction A. The head 3 mills off bone material with the teeth 10, 20, 30, so that the head 3 dips into the bone and a groove is produced in the bone. The head 3 is moved so far in direction Z until the guide surface 5 lies against the milling template. The width of the head 3 corresponds to the width of the slit in the milling template and to the width of the groove to be milled into the bone. The surgical jigsaw with the tool 1 is in addition pushed forward and backward in work direction A until the head 3 has reached the beginning and the end of the slit in the milling template. Hereby, it is ensured that the groove which is milled into the bone corresponds in its length to the length of the slit in the milling template.

The tool 1 and the milling template are coordinated in their dimensions to the tibia implant which is to be inserted. The distance of the lateral surfaces 7 of the head 3 defines its width, which corresponds to the width of the groove which is to be milled. The width of the slit in the milling template can correspond to the width of the head 3, so that the tool 1 is centered and guided via the lateral surfaces 7 in the milling template. When the width of the head 3 is less than the width of the slit in the milling template, the body 2 can contain additional planar centering surfaces 8, which are oriented parallel to the work direction A and perpendicularly to the guide surface 5 and can be guided in a corresponding groove in the milling template.

After the milling of the groove, the head 3 of the tool 1 is directed out from the milled groove and the milling template is removed from the tibia. The tibia implant can be a part of an artificial knee joint and can have an anchoring fin which is then inserted into the milled groove. The preparation of the groove in the tibia is therefore completed after only one working step with the tool 1. If the tibia implant is to be inserted in a cement-free manner, then the groove is milled 0.3 mm narrower than the anchoring fin of the tibia implant. Through the overlap of 0.3 mm, a "press fit" anchoring is achieved, i.e. the tibia implant can be driven into the tibia and is held there securely without further use of cement.

The configuration of the first tooth 10 and of the second tooth 20 at the head 3 of the tool 1 is explained in further detail below with the aid of FIGS. 2 and 3. Each of the teeth 10, 20 contains a first surface 11, 21 for shaving off bone material, which first surface is oriented transversely to the work direction A and is designated as "shaving surface". Each of the teeth 10, 20 contains a second surface 12, 22 for pressing on bone material, which second surface adjoins the shaving surface 21 and is designated as "pressing surface". The shaving surfaces 11, 21, in relation to the work direction A, are more inclined than the pressing surfaces 12, 22. The two teeth 10, 20 are oriented with their shaving surface 11, 21 and their pressing surface 12, 22 opposite each other, such that, during a movement of the head 3 in work direction A, at any one time the shaving surface of the tooth lying ahead in work direction and the pressing surface of the tooth lying therebehind in work direction are in operation. If, for example, the head 3 is moved along the work direction A in FIGS. 2 and 3 from right to left, then the tooth 10 is the tooth lying ahead in work direction A and its shaving surface 11 works and shaves bone material off from the bone. At the same time, the tooth 20 is the tooth lying therebehind in work direction A, wherein its pressing surface 22 works and presses onto the base of the groove bone particles which have been shaven off by the shaving surface 11, so that the bone material is compacted there. On the backward movement of the head 3 in FIGS. 2 and 3 from left to right, the relationships are reversed and the tooth 20 is the tooth lying ahead in work direction A, the shaving surface 21 of which works. At the same time, the tooth 10 is the tooth lying therebehind in work direction A, the pressing surface 12 of which works. On each forward and backward movement of the head 3 therefore bone material is shaven off by one shaving surface lying ahead in work direction A, and shaven off bone material is pressed onto the bone by one pressing surface lying therebehind in work direction A. Hereby, a very precise groove can be milled, wherein the bone surface is compacted by the bone material being pressed on by the pressing surfaces 12, 22.

Each of the teeth 10, 20 contains an edge 13 or respectively 23, formed at the transition from the shaving surface 11 or respectively 21 to the pressing surface 12 or respectively 22, which edge is designated as the "main cutting edge". For the further description of the geometry of the teeth 10 and 20, a reference line 6 is defined, illustrated in dot-and-dash lines, which is a straight line which is applied parallel to the work direction A onto the main cutting edge 13 of the first tooth 10 and the main cutting edge 23 of the second tooth 20. The main cutting edges 13 and 23 therefore lie at the same height H over the guide surface 5. Furthermore, a reference plane is defined, which is oriented parallel to the work direction A and parallel to the feed movement Z. The reference plane therefore lies parallel to the plane of the drawing in FIG. 3 and is, in addition, perpendicular to the guide surface 5. The lateral surfaces 7 of the head 3 are planar surfaces which lie parallel to the reference plane. The distance of the lateral surfaces 7 with respect to one another can be 2 mm to 4 mm.

In a section D adjoining the main cutting edge 13, the pressing surface 12 changes its distance b with respect to the reference line 6 by 0.07 mm to 0.17 mm, in particular by 0.09 mm to 0.16 mm, when the distance b of the pressing surface 12 to the reference line 6 is measured at two locations which are spaced apart from one another by a measurement d of 0.2 mm along the reference line 6. In other words when looking at FIG. 3, when the distance d is 0.2 mm along the reference line 6, the distance b is 0.07 to 0.17 mm (or 0.09 to 0.16 mm). The section D extends from the main cutting edge 13 up to a distance of 1 mm along the reference line 6.

In a section E adjoining the main cutting edge 13, the shaving surface 11 changes its distance f with respect to the reference line 6 by 0.19 mm to 0.2 mm when the distance f of the shaving surface 11 to the reference line 6 is measured at two locations which are spaced apart from one another by a measurement e of 0.2 mm along the shaving surface 11. In other words when looking at FIG. 3, when the distance e is 0.2 mm along the shaving surface, the distance f is 0.19 to 0.2 mm from the reference line 6. The section E extends from the main cutting edge 13 up to a distance of 1 mm along the shaving surface 11.

The shaving surface 11 can, as indicated in dashed lines in FIG. 3 by reference number 11', also be inclined in the other direction in relation to the reference line 6. In particular, the shaving surface 11 can be a planar surface, indicated in dashed lines in FIG. 3 by the reference number 11", which is oriented perpendicularly to the work direction A, so that the distance f changes by 0.2 mm when the distance f of the shaving surface 11 to the reference line 6 is measured at two locations which are spaced apart from one another by the measurement e of 0.2 mm along the shaving surface 11. The shaving surface 11" has the greatest possible inclination to the work direction A. The dimensions described above for the shaving surface 11 and the pressing surface 12, in particular the distances b and f in relation to the reference line 6, apply equally for the shaving surface 21 and the pressing surface 22 of the second tooth 20. The teeth 10 and 20 are mirror-symmetrical to a plane lying perpendicularly to the work direction.

The tooth contour between the main cutting edge 13 of the first tooth 10 and the main cutting edge 23 of the second tooth 20 has a distance B to the reference line 6, which is at most 20% of the distance T measured along the reference line 6 from the main cutting edge 13 of the first tooth 10 to the main cutting edge 23 of the second tooth 20. The distance T is 4 mm to 5 mm, so that with the use of the tool 1 in jigsaws with a stroke between 5 mm and 10 mm a particular site of the bone is always covered by both main cutting edges 13, 23. The stroke of the surgical jigsaw is indicated in FIG. 2 by the measurement S to a head 3, illustrated in dashed lines, which is moved in work direction A. The tool has a total length of approximately 100 mm to 150 mm, wherein the head 3 has a length of 15 mm to 20 mm and a width of 2 mm to 4 mm.

The pressing surface 12 and the pressing surface 22 are (mutually, together) curved in a concave manner with a radius of curvature R. The pressing surface 12 continues in a kink-free manner into the pressing surface 22. The pressing surface 12 and 22 is formed by the surface of a circular cylinder with a diameter of 7 mm to 11 mm. The radius of curvature R is then 3.5 mm to 5.5 mm. The center line of the circular cylinder lies perpendicularly to the work direction A and, at the same time, perpendicularly to the reference plane. The pressing surfaces 12, 22 run perpendicularly to the reference plane. The main cutting edges 13 and 23 run in a straight line perpendicularly to the work direction A and perpendicularly to the reference plane. The outer contour of the head 3 is semi-circular in a view perpendicularly onto the reference plane. Hereby, the head 3 is optimally adapted to the anchoring fin of a tibia implant, which has at its front and rear end a radius which can correspond to the radius of the semicircle surrounding the main cutting edges of the head 3.

The additional teeth 30 can have respectively in the same manner a shaving surface and a pressing surface and the same shape as the teeth 10 and 20. They exert their shaving and pressing function in particular when the head 3 is fed into the bone with a feed movement Z which is not oriented perpendicularly to the guide surface 5. The reference line in relation to two teeth 30 lying one behind the other is applied here in the reference plane, remaining unchanged, onto the main cutting edges of these two teeth 30, so that it no longer runs parallel to the work direction A. The dimensions R, T, B, b and f can then be determined in an analogous manner in relation to the differently lying reference line.

A tool which is particularly suited for the preparation of a tibia groove for inserting the tibial portion of the Oxford knee system has a distance T of 5 mm, a radius R of 4 mm, a height H of the two main cutting edges 13 and 23 of 12.8 mm. The distance of the planar lateral surfaces is 2.8 mm for a fit-and-fill-cemented anchoring and 2.5 mm for a press fit cement-free anchoring. The planar shaving surfaces 11" and 21" here are perpendicular to the reference line 6.

REFERENCE DESIGNATIONS 1 tool
2 body
3 head
4 holder area
5 guide surface
6 reference line
7 lateral surfaces
8 centering surfaces 10 first tooth
11 shaving surface
12 pressing surface
13 main cutting edge
20 second tooth
21 shaving surface
22 pressing surface
23 main cutting edge
30 further teeth
A work direction
B distance
D section
E section
R radius of curvature
S stroke
T distance
Z feed movement
b distance
d measurement
e measurement
f distance

What is claimed is:

1. A tool for insertion into a surgical jigsaw, the tool comprising:
an elongated body with a longitudinal direction, wherein at a first end of the body a head of the tool is arranged, and wherein at a second end of the body a holder area being adapted to a tool holder of a surgical jigsaw is arranged, wherein the holder area of the tool is movable by the surgical jigsaw in a work direction oriented parallel to the longitudinal direction of the body;
wherein the head is adapted for milling a groove into bone material and has at least a first tooth and a second tooth arranged behind one another in the work direction;
wherein each of the teeth has a shaving surface, which is oriented transversely to the work direction and is adapted for shaving off bone material;
wherein each of the teeth has a pressing surface, which adjoins the shaving surface and is adapted for pressing on bone material;
wherein each of the teeth contains a main cutting edge formed at a transition from the shaving surface to the pressing surface;
wherein a width of one of the main cutting edges transversely to the work direction corresponds to a width of the groove to be milled;
wherein the shaving surface, in relation to the work direction, is more inclined than the pressing surface; and
wherein the at least first tooth and second tooth are oriented with their shaving surface and their pressing surface opposite each other, wherein during a movement of the head in the work direction at any one time the shaving surface of the tooth lying ahead in the work direction and the pressing surface of the tooth lying therebehind in the work direction are in operation.

2. The tool according to claim 1, wherein the pressing surface of the first tooth and the pressing surface of the second tooth are curved in a concave manner.

3. The tool according to claim 1, wherein the main cutting edge of the first tooth runs parallel to the main cutting edge of the second tooth.

4. The tool according to claim 1, wherein a reference line is defined as a straight line which is applied parallel to the work direction onto the main cutting edge of the first tooth and/or the main cutting edge of the second tooth, wherein the pressing surface in a section adjoining the main cutting edge changes its distance with respect to the reference line at most by 0.2 mm, when the distance of the pressing surface to the reference line is measured at two locations which are spaced apart from one another by 0.2 mm along the reference line.

5. The tool according to claim 1, wherein a reference line is defined as a straight line which is applied parallel to the work direction onto the main cutting edge of the first tooth and/or the main cutting edge of the second tooth, wherein the shaving surface in a section adjoining the main cutting edge changes its distance with respect to the reference line at least by 0.18 mm, when the distance of the shaving surface to the reference line is measured at two locations which are spaced apart from one another by 0.2 mm along the first shaving surface.

6. The tool according to claim 1, wherein a reference line is defined as a straight line which is applied parallel to the work direction onto the main cutting edge of the first tooth and/or the main cutting edge of the second tooth, wherein a tooth contour between the main cutting edge of the first tooth and the main cutting edge of the second tooth has a distance with respect to the reference line which is at most 25 percent of the distance, measured along the reference line, from the main cutting edge of the first tooth to the main cutting edge of the second tooth.

7. The tool according to claim 1, including a guide surface for delimiting a milling depth of the tool in the bone material, where the head of the tool projects over the guide surface and the guide surface is oriented parallel to the work direction.

8. The tool according to claim 1, wherein a width of the head of the tool is delimited by a first lateral surface opposite a second lateral surface, wherein the width of the head between the lateral surfaces is the same as the width of one of the main cutting edges, wherein the lateral surfaces are perpendicular to the guide surface and wherein the lateral surfaces are planar lateral surfaces.

9. The tool according to claim 1, wherein a distance of the main cutting edge of the first tooth to the main cutting edge of the second tooth measured parallel to the work direction is at most as great as a working stroke of the surgical jigsaw for which the tool is intended.

10. The tool according to claim 1, wherein the tool is authorized for multiple surgical use.

11. The tool according to claim 1, wherein the head at the first end of the body is the only head.

12. The tool according to claim 1, wherein the first end of the body does not have a second head.

13. The tool according to claim 1, wherein a reference line is defined as a straight line which is applied parallel to the work direction onto the main cutting edge of the first tooth and/or the main cutting edge of the second tooth, wherein a tooth contour between the main cutting edge of the first tooth and the main cutting edge of the second tooth has a distance with respect to the reference line which is at most 20 percent of the distance, measured along the reference line, from the main cutting edge of the first tooth to the main cutting edge of the second tooth.

14. The tool according to claim 1, wherein a reference line is defined as a straight line which is applied parallel to the work direction onto the main cutting edge of the first tooth and/or the main cutting edge of the second tooth, wherein a tooth contour between the main cutting edge of the first tooth and the main cutting edge of the second tooth has a distance with respect to the reference line which is at most 10 percent of the distance, measured along the reference line, from the main cutting edge of the first tooth to the main cutting edge of the second tooth.

15. The tool according to claim 1, wherein the first tooth and the second tooth are disposed parallel to the longitudinal direction.

16. The tool according to claim 1, wherein the first tooth and the second tooth are not offset to one another as seen along the work direction.

17. A method for milling a groove in a bone with a tool inserted into a surgical jigsaw, the method comprising the steps of:

providing the tool comprising:

an elongated body with a longitudinal direction, wherein at a first end of the body a head of the tool is arranged, and wherein at a second end of the body a holder area being adapted to a tool holder of a surgical jigsaw is arranged, wherein the holder area of the tool is movable by the surgical jigsaw in a work direction oriented parallel to the longitudinal direction of the body;

wherein the head has at least a first tooth and a second tooth arranged behind one another in the work direction;

wherein each of the teeth has a shaving surface, which is oriented transversely to the work direction and is adapted for shaving off bone material;

wherein each of the teeth has a pressing surface, which adjoins the first shaving surface and is adapted for pressing on bone material;

wherein each of the teeth contains a main cutting edge formed at a transition from the shaving surface to the pressing surface;

wherein the shaving surface, in relation to the work direction, is more inclined than the pressing surface; and wherein the at least first tooth and second tooth are oriented with their shaving surface and their pressing surface opposite each other, milling the groove in the bone by moving the head in linear oscillation forward and backward by the surgical jigsaw along the work direction, wherein during the forward movement of the head the shaving surface of the first tooth, lying ahead in the work direction shaves off bone material and the pressing surface of the second tooth, lying behind the shaving surface of the first tooth in the work direction, presses bone material onto the bone, and wherein during the backward movement of the head the shaving surface of the second tooth lying ahead in the work direction shaves off bone material and the pressing surface of the first tooth, lying behind the shaving surface of the second tooth in the work direction, presses bone material onto the bone, wherein a width of the groove corresponds to a width of one of the main cutting edges transversely to the work direction.

\* \* \* \* \*